United States Patent [19]

Tsuji et al.

[11] Patent Number: 5,569,795
[45] Date of Patent: Oct. 29, 1996

[54] FLUORINATION CATALYST AND FLUORINATION PROCESS

[75] Inventors: Katsuyuki Tsuji; Kimitaka Oshiro; Tetsuo Nakajo, all of Kawasaki, Japan

[73] Assignee: Showa Denko K. K., Tokyo, Japan

[21] Appl. No.: 554,836

[22] Filed: Nov. 7, 1995

Related U.S. Application Data

[62] Division of Ser. No. 262,496, Jun. 20, 1994, Pat. No. 5,494,876.

[30] Foreign Application Priority Data

Jun. 18, 1993 [JP] Japan ................................. 5-147897

[51] Int. Cl.$^6$ ................................ C07C 17/20; C07C 19/08
[52] U.S. Cl. .................................................... 570/168
[58] Field of Search ........................................... 570/168

[56] References Cited

U.S. PATENT DOCUMENTS

| | | | |
|---|---|---|---|
| 3,992,325 | 11/1976 | Knaak | 252/442 |
| 4,155,881 | 5/1979 | Sullivan | 252/441 |
| 4,465,786 | 8/1984 | Zimmer et al. | 502/169 |
| 4,922,037 | 5/1990 | Manzer . | |
| 5,008,474 | 4/1991 | Walraevens et al. | 570/168 |

FOREIGN PATENT DOCUMENTS

| | | |
|---|---|---|
| 0295885 | 12/1988 | European Pat. Off. . |
| 502605 | 9/1992 | European Pat. Off. . |
| 516000 | 12/1992 | European Pat. Off. . |
| 2095438 | 4/1990 | Japan . |
| 2172933 | 7/1990 | Japan . |
| 4346943 | 12/1992 | Japan . |

*Primary Examiner*—Joseph E. Evans
*Attorney, Agent, or Firm*—Sughrue, Mion, Zinn, Macpeak & Seas

[57] ABSTRACT

A fluorination catalyst comprising indium, chromium, oxygen and fluorine as essential constituent elements thereof. The catalyst is prepared by fluorinating a catalyst precursor comprising indium and chromium elements by bringing it into contact with hydrogen fluoride or a fluorine-containing halogenated hydrocarbon at a temperature of 300° to 500° C. A halogenated hydrocarbon is fluorinated by bringing it into contact with hydrogen fluoride in a gaseous phase in the presence of the catalyst.

17 Claims, No Drawings

1

FLUORINATION CATALYST AND FLUORINATION PROCESS

This is a divisional of application Ser. No. 08/262,496 filed Jun. 20, 1994 now U.S. Pat. No. 5,494,876.

BACKGROUND OF THE INVENTION

1. Field of the Invention

This invention relates to a fluorination catalyst and a fluorination process. More particularly, the invention relates to an improved fluorination catalyst for producing a hydrofluorocarbon (hereinafter referred to as "HFC") at a high yield and a process for efficiently producing the HFC with high productivity by bringing hydrogen fluoride into contact with a halogenated hydrocarbon in a gaseous phase by using the fluorination catalyst, when the HFC, which precludes the possibility of destruction of the ozone layer because it does not contain chlorine in the molecule thereof, particularly difluoromethane (hereinafter referred to as "HFC-32"), 1,1,1,2-tetrafluoroethane (hereinafter referred to as "HFC-134a") and pentafluoroethane (hereinafter referred to as "HFC-125"), is produced.

2. Description of the Related Art

Typical industrial production processes for an HFC, according to the prior art, include a process which brings a hydrogen-containing halogenated hydrocarbon into contact with HF and converts halogens such as chlorine, bromine and iodine into fluorine (in some cases, by using an unsaturated halogenated hydrocarbon as a raw material, reactions to add HF and convert halogens such as chlorine, bromine and iodine, into fluorine may simultaneously occur), and a process which brings a halogenated hydrocarbon into contact with $H_2$ and exchanges the halogens, such as chlorine, bromine and iodine (although some fluorine atoms, in some cases) with H. Among these reactions, the fluorination reaction of a hydrogen-containing halogenated hydrocarbon with HF does not proceed smoothly in many cases, and the production quantity of the HFC depends greatly on the catalyst used.

A typical example of an unsmooth reaction is the synthesizing reaction of HFC-134a by fluorination of 1-chloro-2,2,2-trifluoroethane (hereinafter referred to as "HCFC-133a"). This reaction is an endothermic reaction which is thermodynamically disadvantageous. For this reason, the reaction is generally carried out by adding HF in an amount exceeding a stoichiometric amount to HCFC-133a and other reaction conditions (pressure, temperature, space velocity) are chosen to provide a significant conversion ratio of HCFC-133a. By way of example, Japanese Unexamined Patent Publication (Kokai) No. 55-27138 obtains HFC-134a at a yield of 32% using a compound obtained by treating $CrF_3 \cdot 3H_2O$ with air as the catalyst under a reaction condition where the reaction pressure is atmospheric pressure, the reaction temperature is 400° C., a molar ratio of HF to HCFC-133a (hereinafter called the molar ratio) is 8 and the space velocity (hereinafter abbreviated to SV) is 550 $h^{-1}$. U.S. Pat. No. 4,922,037 obtains HFC-134a at a yield of 32% using a catalyst obtained by fluorinating $CoCl_2/Al_2O_3$, under a reaction condition where the pressure is atmospheric pressure, the temperature is 410° C., the molar ratio is 10 and the contact time is 30 seconds (SV 48 $h^{-1}$). The reaction at such a low SV provides low productivity, and the reaction at the high temperature invites not only a heat energy loss but also the drop of selectivity. Furthermore, according to the studies of the present inventors, it invites a reduction in catalyst life. Accordingly, various studies have been made to attain higher activity of the catalyst and to prolong its service life. Japanese Unexamined Patent Publication (Kokai) No. 2-172933, for example, discloses that a catalyst comprising a halide or an oxide containing Cr and at least one element selected from the group consisting of Al, Mg, Ca, Ba, Sr, Fe, Ni, Co and Mn, and Cr, has high durability (life). EP 502605 teaches that a Cr-containing catalyst supporting Zn exhibits high activity. Further, European Patent Publication No. 516000-A1 describes that a catalyst comprising partially fluorinated $Cr_2O_3$ supporting Ru and Pt has long life.

As a catalyst using a component other than Cr as the principal component, the Applicant of the present invention proposed in Japanese Unexamined Patent Publication (Kokai) No. 2-95438 a catalyst which contains an In compound supported on a support such as alumina, and is treated by HF. However, activity of this catalyst is lower than that of the catalysts using Cr as the principal component.

As described in the specification of Japanese Unexamined Patent Publication (Kokai) No. 4-346943, however, it has been clarified that when the fluorination reaction for HCFC-133a with HF is carried out using the Cr-containing or Al-containing catalyst according to the prior art, a new problem inherent to this reaction occurs, in that the reaction rate falls and productivity drops when the reaction pressure is elevated. In other words, even in the case of a catalyst which provides a high yield at atmospheric pressure, the yield drops remarkably because the conversion of HCFC-133a drops when the reaction pressure is elevated (to 10 $kg/cm^2G$ (gauge pressure), for example), even though selectivity to HFC-134a can be somewhat improved. (Other conditions such as the reaction temperature, the molar ratio, SV converted to the standard state, etc, are kept the same for the purpose of comparison). This phenomenon can be likewise observed in the fluorination reaction of other hydrogen-containing halogenated hydrocarbons, though the degree is somewhat different.

When the reaction is carried out at an atmospheric pressure of about 1 $kg/cm^2G$ in practical production equipment, additional equipment becomes necessary to reduce the pressure of the reactor, and this results in an undesirable increase in the cost. Further, performing the reaction at an elevated pressure provides higher selectivity and it can particularly restrict the production of unsaturated compounds, having high toxicity, as by-products. Accordingly, development of a catalyst which does not cause the reaction rate to fall even when the reaction pressure is elevated and further preferably, a catalyst which increases the reaction rate when the reaction pressure is elevated, has been desired.

Low activity of the catalyst, and a short service life, that have been problems in the prior art, are also improved by the present invention because they greatly contribute to the catalyst cost and productivity.

SUMMARY OF THE INVENTION

As a result of intensive studies, the present inventors have found that the negative effect of pressure on the reaction rate can be improved by combining In and Cr as metalic elements. Thus, the present inventions have accomplished the objectives of the present invention.

It is a primary object of the present invention to provide an improved fluorination catalyst for the production of an HFC at a high yield.

It is another object of the present invention to provide a process for producing an HFC, such as HFC-32, HFC-134a or HFC-125, with high productivity, by bringing a halogenated hydrocarbon into contact with hydrogen fluoride in a gaseous phase.

Thus, the present invention provides a fluorination catalyst comprising indium, chromium, oxygen and fluorine as essential constituent elements thereof.

The catalyst may be prepared by a process comprising fluorinating a catalyst precursor comprising indium and chromium elements by bringing it into contact with hydrogen fluoride or a fluorine-containing halogenated hydrocarbon at a temperature of 300° to 500° C.

The present invention also provides a process for fluorinating a halogenated hydrocarbon comprising bringing a halogenated hydrocarbon into contact with hydrogen fluoride in a gaseous phase in the presence of a fluorination catalyst as set forth above.

DESCRIPTION OF THE PREFERRED EMBODIMENTS

In the catalyst of the present invention, an atomic ratio of indium to chromium is preferably from 0.005 to 0.6, more preferably from 0.01 to 0.5, especially from 0.01 to 0.3.

It is preferred that large quantities (in the order of percent by weight) of alkali metals are not contained as the constituent elements of the catalyst other than In, Cr, O and F, but other metallic elements may be contained in an amount of several (one digit) percent or less. Particularly, at least one element selected from the group consisting of the elements of Groups 11, 12, 13 and 14 (new group name approved by IUPAC) of the Long Form Periodic Table, among others, Cu, Ag, Au, Zn, Cd, Hg, Al, Ga, Sn, Pb, etc., may be contained within the range where their atomic ratios to Cr are from 0.001 to 0.5, preferably from 0.003 to 0.1, as a promotor which is expected to provide a life extending effect on the catalyst.

The catalyst according to the present invention can be prepared by using an In- and Cr-containing compound (e.g. oxide or hydroxide) as a catalyst precursor, fluorinating the catalyst precursor with HF, $F_2$ or a halo-generated hydrocarbon containing fluorine in the molecule thereof, to partially replace O and/or OH by F. The In- and Cr-containing compound can be supported on a support, and examples of the suitable support are active carbon, alumina, aluminum fluoride, calcium fluoride, magnesium fluoride, and so forth.

To prepare the catalyst precursor, any known methods such as a kneading method, an impregnation method, a coprecipitation method, etc., can be used, and any compounds can be used as the starting materials for preparing the catalyst precursor as long as they are available on an industrial scale. Among them, the impregnation method and the coprecipitation method are preferred because they can uniformly distribute In and Cr. Particularly because the coprecipitation method can uniformly regulate even the bulk composition (not only the surface composition) of the catalyst, it is further preferred. Accordingly, a preferred example of the preparation method of the catalyst precursor comprises the steps of reacting a solution, having dissolved therein In and Cr compounds, with a precipitant to form a slurry, and then conducting filtration, washing and drying and calcination (an example of the coprecipitation method). Another preferred example comprises the steps of causing chromium oxide or chromium hydroxide to be impregnated with a solution of the In compound, and then conducting drying and calcination (example of the impregnation method). When a support is used, the support is caused to be impregnated with a solution containing the In and Cr compounds, and then conducting drying and calcination.

Still another preferred example of a coprecipitation method is as follows. A solution containing the In and Cr compounds and a precipitant are dropped either simultaneously or alternately into the reaction vessel while the pH of the reaction solution is kept to be from 6 to 12, particularly preferably from 6.5 to 10 by controlling the dropping rate, to form a slurry, and the resulting slurry is filtered, washed, dried and calcined.

Nitrates, chlorides and sulfates are preferably used as the In and Cr compounds. Among them, nitrates are preferred in the case of the coprecipitation method, and chlorides are preferred in the impregnation method. Preferred examples of the precipitant are ammonia, sodium hydroxide, sodium carbonate, sodium hydrogencarbonate, potassium hydroxide, potassium carbonate, potassium hydrogencarbonate, ammonium carbonate and ammonium hydrogencarbonate. Among them, ammonia is particularly preferred.

When a molded article is desired as the form of the catalyst, it is possible to conduct tablet-molding before, or after, calcination, or to conduct extrusion molding before drying.

Drying is carried out at a temperature within the range of 80° to 130° C., particularly from 90° to 120° C., in an atmosphere of air or an inert gas such as $N_2$, for at least 30 minutes, but other drying methods such as vacuum drying can also be employed.

Calcination is suitably carried out at a temperature within the range of 300° to 600° C., preferably from 350° to 500° C., but depending on the preparation method, the calcination atmosphere must be selected. In other words, when the chromium compounds such as chromium hydroxide, chromium oxide, etc., come into contact with $O_2$ at a high temperature of not less than about 350° C., a drastic drop of the specific surface area is induced, and active carbon starts to burn and partially disappears. Accordingly, when the chromium compound is used as the principal component of the catalyst precursor without using the support or when active carbon is used as the support, the catalyst must not be exposed in an atmosphere, containing $O_2$ at 1,000 Pa (absolute pressure) at a temperature of more than 350° C., and calcination is preferably carried out in the atmosphere of an inert gas such as $N_2$, Ar, etc., or a reducing gas. The term "reducing gas atmosphere" hereby used represents an atmosphere containing a gas having reducing ability such as $H_2$, CO, NO, and so forth, and may include inert gases and/or water vapour. An oxidizing gas such as $O_2$ may be added if its concentration remains at a level such that no safety problem occurs, but it is more preferred that an oxidizing gas is not practically contained.

When alumina and various metal fluorides are used as the support, the drop of the specific surface area of the catalyst can be prevented even in the $O_2$ atmosphere at a high temperature. Therefore, calcination can be done in an $O_2$-containing atmosphere, most typically, in air. However, as described in Japanese Unexamined Patent Publication (Kokai) No. 5-92141, a problem occurs in that some compounds of Cr are scattered and removed from the precursor or catalyst at the time of fluorination of the precursor. Accordingly, when the support described above is used, calcination is carried out in the inert gas or reducing gas atmosphere. Alternatively, it is preferred to carry out calcination first in an $O_2$-containing atmosphere and then in a reducing gas atmosphere.

A further preferred calcination method is the one that includes a heat-treatment step, in a reducing gas atmosphere, in the calcination process. In other words, when the chromium compound is used as the principal component of the catalyst precursor or when active carbon is used as the support, calcination in a reducing gas atmosphere is preferably carried out immediately after the drying step, or after calcination in the inert gas atmosphere is carried out, further calcination in the reducing gas atmosphere is preferably carried out further. When alumina and various other metal fluorides are used as the support, it is preferred to carry out calcination in the reducing gas atmosphere immediately after the drying step, or to carry out further calcination in the reducing gas atmosphere after calcination is carried out in the inert gas or in the $O_2$-containing atmosphere.

Heat-treatment in the reducing gas atmosphere is expected to provide effects such as a decrease in the amount of scattering of Cr compounds during fluorination of the precursor before the reaction is conducted, an improvement in the activity of the catalyst, and so forth. The temperature for heat-treatment is suitably from 350° to 500° C., preferably from 370° to 460° C., and most preferably from 370° to 450° C. The kind of reducing gas to be used is $H_2$, CO, NO, etc., but $H_2$ can be used appropriately because it is easy to handle. The concentration of the reducing gas is from 0.1 to 100 vol %. Up to 20 vol % of water and up to 99.9 vol % of an inert gas can be mixed in the reducing gas, whenever necessary, but the $O_2$ concentration must be limited to be not greater than 0.1 vol % from the aspect of safety. The gas flow rate is suitably from 10 to 10,000 $h^{-1}$ in terms of GHSV (converted to the standard state), and the pressure is preferably from the atmospheric pressure to 10 kg/cm$^2$G because is easy. The time for treatment is at least 30 minutes, and preferably from 1 to 10 hours.

It is not preferred to expose the catalyst precursor, which is heat-treated in the reducing gas atmosphere, to a high temperature in an atmosphere containing $O_2$ at an absolute pressure of more than 1,000 Pa. Therefore, further calcination in the $O_2$-containing atmosphere such as in the air should be avoided after calcination is carried out in the reducing gas atmosphere. When the pressure is released so as to remove the catalyst precursor after calcination in the reducing gas atmosphere is completed, an operation which introduces $O_2$ into the system at a temperature of more than 200° C. should be likewise avoided. In other words, air should be introduced little by little into the system at a temperature of less than 150° C., more preferably less than 120° C. so as to gradually increase the $O_2$ concentration inside the system, and thereafter air should be introduced.

The catalyst precursor may be prepared by the method described above or by any known methods, but the atomic ratio of In to Cr (hereinafter called the "In/Cr ratio") must be within the range of 0.005 to 0.6, preferably 0.01 to 0.5 and particularly preferably 0.01 to 0.3. If the In/Cr ratio is smaller than the range described above, the drop of the reaction rate due to an increase in the reaction pressure becomes large, and if the In/Cr ratio is too great, on the contrary, the reaction rate is again likely to drop even under the atmospheric pressure. The In/Cr ratio can be easily regulated by adjusting the proportion of powder to be mixed in the case of the kneading method, and by controlling the concentration of the In and/or Cr compounds in the solution in the cases of the impregnation method and the coprecipitation method.

The fluorination catalyst according to the present invention requires further O and F as the indispensable constituent elements. The suitable ranges of O and F change in accordance with the In/Cr ratio and with the preparation method of the catalyst precursor, but each of these elements must exist in an amount of at least 0.3 wt % on the basis of the total weight of the catalyst. A preferred range of the O content is from 1 to 25 wt %. The O and the F can be contained in the catalyst by fluorinating the In- and Cr-containing compound by HF, $F_2$ or a halogenated hydrocarbon having F in the molecule thereof, as described above. Fluorination using HF is excellent among them from the aspect of the cost.

The fluorination temperature is preferably from 300° to 500° C., particularly preferably from 300° to 450° C. The concentration of the fluorinating agent such as HF is from 0.1 to 100 vol %, but the agent is preferably diluted, by an inert gas such as $N_2$, so that the temperature rise due to the heat of reaction (hereinafter abbreviated to "$\Delta T$") is at most 50° C. The gas flow rate is suitably from 10 to 10,000 $h^{-1}$ in terms of GHSV, and the pressure is from the atmospheric pressure to 20 kg/cm$^2$G.

A preferred example of the fluorination method for the catalyst precursor is as follows. First, to start the fluorination reaction, HF and $N_2$ are supplied at atmospheric pressure and at a temperature of 300° to 400° C. in such a fashion that the HF concentration attains 5 to 30 vol %. After a hot spot passes through a precursor packing layer, the HF concentration and the pressure are elevated to at least 90 vol % and to 2 to 10 kg/cm$^2$G, respectively, while attention is paid to $\Delta T$. The treatment is continued under the final condition at least until $\Delta T$ no longer occurs.

Calcination of the catalyst precursor and its fluorination can be carried out using the same reactor if the reactor is a product of Inconel Co. or Hastelloy Co, and the operation is easy in such a case.

The fluorination catalyst according to the present invention, which contains In, Cr, O and F as the indispensable constituent elements, can be applied to fluorination of halogenated hydrocarbons with HF, and is particularly effective for carrying out the fluorination reaction of the hydrogen-containing halogenated hydrocarbons at an elevated pressure. In other words, the catalyst of the present invention can overcome the negative effect of reaction pressure on the reaction rate and conversion of the starting hydrocarbon seen when a conventional fluorination catalyst, e.g. chromium oxyfluoride, is employed.

The effect described above will be explained in further detail. The catalyst of the present invention containing In, Cr, O and F as the indispensable constituent elements exhibits a catalytic activity which is equal to, or somewhat higher than, that of the conventional fluorination catalyst such as chromium oxyfluoride at a pressure near the atmospheric pressure. Nonetheless, the catalyst of the invention is almost free from the drop of the reaction rate (conversion of the starting hydrocarbon) even when the reaction pressure is elevated. On the other hand, in the conventional fluorination catalyst such as chromium oxyfluoride, the reaction rate becomes lower with a higher reaction pressure. Accordingly, the difference in the conversion ratios becomes greater between the present catalyst and the conventional fluorination catalyst when the reaction pressure becomes higher.

In other words, the use of the present catalyst can overcome the negative effect of the reaction pressure which is observed in the conventional fluorination catalyst. Because the quantities of by-products can be reduced by effecting the reaction at an elevated pressure, HFC can be obtained at a higher yield particularly in the fluorination reaction of the hydrogen-containing halogenated hydrocarbons at an elevated pressure.

The term "hydrogen-containing halogenated hydrocarbon" used in the present invention mainly represents those halogenated hydrocarbons which contain H in the molecules of C1 to C4, and examples of such halogenated hydrocarbons are $CHCl_3$, $CH_2Cl_2$, $CH_2FCl$, $CH_3Cl$, $C_2HCl_3$, $C_2H_2Cl_2$, $C_2H_3Cl$, $C_2HCl_5$, $C_2HFCl_4$, $C_2HF_2Cl_3$, $C_2HF_3Cl_2$, $C_2HF_4Cl$, $C_2H_2F_3Cl$, $C_2H_3Cl_3$, $C_2H_3FCl_2$, $C_2H_3F_2Cl$, $C_2H_4Cl_2$, $C_2H_4FCl$, $C_2H_5Cl$, $C_3H_2F_4Cl_2$, and $C_3HF_4Cl_3$. Furthermore, in the hydrocarbons described above, all or some of the Cl atoms may be substituted by Br and I.

The catalyst of the present invention is effective in the fluorination reaction of $CH_2Cl_2$, $CH_2FCl$ (HCFC-31), $CHCl=CCl_2$ (trichloroethylene), $CF_2CH_2Cl$ (HCFC-133a), $CCl_2=CCl_2$ (perchloroethylene), $CF_3CHCl_2$ (HCFC-123) and $CF_3CHFCl$ (HCFC-124), as the synthesis route of HFC-32, HFC-134a and HFC-125, which draw attention as HFCs free from the ability to destroy the ozone layer. The catalyst of the present invention is particularly effective for the production of HFC-134a by fluorination of HCFC-133a.

The fluorination reaction can employ a reaction means such as a fixed bed, a fluidized bed, a moving bed, etc., but the fixed bed is generally used. A suitable reaction condition varies with the reaction. However, a molar ratio of HF is generally 0.5 to 20 to the halogenated hydrocarbon, the temperature is generally 200° to 400° C., the pressure is generally from the atmospheric pressure to 20 kg/cm$^2$G, and SV is generally 50 to 100,000 h$^{-1}$. When the fluorination catalyst of the present invention is used, productivity does not drop even at an elevated pressure. Therefore, the reaction pressure may be elevated above the atmospheric pressure, and is preferably 1 to 20 kg/cm$^2$G and more preferably 1.5 to 20 kg/cm$^2$G.

Hereinafter, the present invention will be explained in more detail with reference to Examples and Comparative Examples thereof. Needless to say, however, these Examples are merely illustrative but in no way limit the invention. Incidentally, the term "In/Cr ratio" in the following description represents an atomic ratio of each element contained in a catalyst determined by chemical analysis, and the term "molar ratio" in Reaction Examples represents the molar ratio of HF to halogenated hydrocarbons. Further, symbol "SV" represents a value converted to a standard state, and the term "pressure" means gauge pressure.

PREPARATION EXAMPLE 1

A solution of 452 g of $Cr(NO_3)_3.9H_2O$ and 42 g of In $(NO_3)_3.nH_2O$ (where n is about 5) in 1.2 l of pure water and 0.3 l of 28 wt % of aqueous ammonia were added dropwise with stirring into a 10 l container containing therein 600 ml of pure water in the course of about one hour, while their flow rates were being controlled so that a pH of the reaction solution was within the range of 7.5 to 8.5. The resulting slurry of hydroxides was filtered, was well-washed with pure water, and was dried at 120° C. for 12 hours. The resulting solid was ground, mixed with graphite and pelletized by a tableting machine. The pellet was calcinated at 400° C. for 4 hours in a $N_2$ stream to form a catalyst precursor, and 60 ml of this catalyst precursor was packed into an Inconel reaction tube of and was subjected to fluorination treatment first at 350° C. in an HF stream diluted by $N_2$ at an atmospheric pressure, then in a 100 % HF stream not diluted by $N_2$ at 350° C., and further in a 100 % HF stream at an elevated pressure of 4 kg/cm$^2$. The composition of the pellet after this treatment is listed below.

In: 10.8 wt %, Cr: 49.0 wt %
O: 15.1 wt %, F: 23.9 wt %
The In/Cr ratio was found to be 0.1 from these values.

COMPARATIVE PREPARATION EXAMPLE 1

A catalyst precursor not containing In was prepared in the same way as in Preparation Example 1 except that In $(NO_3).nH_2O$ was not added. 60 ml of this catalyst precursor was packed into an Inconel reaction tube of and was subjected to fluorination treatment in the same way as in Preparation Example 1. The composition of the pellet after this treatment is listed below.

Cr: 56.9 wt %, O: 16.3 wt %, F: 23.8 wt %

PREPARATION EXAMPLE 2

200 g of the dry product obtained by Comparative Preparation Example 1 was caused to be impregnated with a solution of 17 g of $InCl_3.4H_2O$ dissolved in pure water, and was again dried at 120° C. The subsequent procedures up to the fluorination treatment were followed in the same way as in Preparation Example 1. The composition of the pellet after this treatment is listed below.

In: 3.7 wt %, Cr: 53.6 wt %
O: 16.0 wt %, F: 23.3 wt %
The In/Cr ratio was found to be 0.03 from these values.

PREPARATION EXAMPLE 3

100 ml of the pellet tableted in Preparation Example 1 was packed into a glass tube, and was calcinated at 400° C. for 4 hours in an $H_2$ stream containing 3 vol % of water vapor to form a precursor. The subsequent procedures up to the fluorination treatment were followed in the same way as in Preparation Example 1.

PREPARATION EXAMPLE 4

111 g of $CrCl_3.6H_2O$ and 6 g of $InCl_3.4H_2O$ were dissolved in 78 g of pure water, and 100 g of high purity active alumina was immersed in the solution to absorb the whole quantity of the solution. After this alumina was dried at 120° C. for 10 hours, it was packed into a glass tube, and was calcinated first at 400° C. for 3 hours in an air stream and then at 400° C. for 4 hours in an $H_2$ stream containing 3 vol % of water vapor. The subsequent procedures up to the fluorination treatment were followed in the same way as in Preparation Example 1. The composition after this treatment is listed below.

In: 1.1 wt %, Cr: 10.5 wt %, Al: 29.0 wt %
O: 2.5 wt %, F: 60.3 wt %

PREPARATION EXAMPLE 5

A pellet was produced in the same way as in Preparation Example 1 except that 1 g of $Cu(NO_3)_2.3H_2O$ was further added to the aqueous solution of $Cr(NO_3)_3.9H_2O$ and $In(NO_3)_3.nH_2O$, and the subsequent procedures up to the fluorination treatment were followed in the same way as in Preparation Example 3.

PREPARATION EXAMPLE 6

A pellet was produced in the same way as in Preparation Example 1 except that 1 g of $Cd(NO_3)_2.4H_2O$ was further added to the aqueous solution of $Cr(NO_3)_3.9H_2O$ and $In(NO_3)_3.nH_2O$, and the subsequent procedures up to the fluorination treatment were followed in the same way as in Preparation Example 3.

PREPARATION EXAMPLE 7

A pellet was produced in the same way as in Preparation Example 1 except that 1 g of $Pb(NO_3)_2$ was further added to the aqueous solution of $Cr(NO_3^-)_3.9\ H_2O$ and $In(NO_3)_3.nH_2O$, and the subsequent procedures up to the fluorination treatment were followed in the same way as in Preparation Example 3.

PREPARATION EXAMPLE 8

A pellet was produced in the same way as in Preparation Example 1 except that 1 g of $AgNO_3$ was further added to the aqueous solution of $Cr(NO_3)_3.9H_2O$ and $In(NO_3)_3.nH_2O$, and the subsequent procedures up to the fluorination treatment were followed in the same way as in Preparation Example 3.

REACTION EXAMPLE 1

Fluorination reaction of HCFC-133a with HF was carried out by packing 50 ml of the catalyst prepared in Preparation Example 1 into an Inconel reaction tube under the following reaction condition. An outlet gas of the reaction tube was blown into a trap of an aqueous KOH solution, and unreacted HF and resulting HCl were removed. The gas composition was analyzed by gas chromatography. Table 1 shows the results at sixth to eighth hours from the start of the reaction.

temperature: 320° C.,
pressure: atmospheric pressure
molar ratio: 8, SV: 1,500 $h^{-1}$

REACTION EXAMPLE 2

The fluorination reaction of HCFC-133a was carried out in the same way as in Reaction Example 1 except that the reaction pressure was set to 4 $kg/cm^2G$. The results are shown in Table 1.

COMPARATIVE REACTION EXAMPLE 1

The fluorination reaction of HCFC-133a was carried out in the same way as in Reaction Example 1 except that the catalyst prepared in Comparative Preparation Example 1 was used. The results are shown in Table 1.

COMPARATIVE REACTION EXAMPLE 2

The fluorination reaction of HCFC-133a was carried out in the same way as in Comparative Reaction Example 1 except that the reaction pressure was set to 4 $kg/cm^2G$. The results are shown in Table 1.

REACTION EXAMPLE 3

The fluorination reaction of HCFC-133a was carried out in the same way as in Reaction Example 1 except that the catalyst prepared in Preparation Example 2 was used. The results are shown in Table 1.

REACTION EXAMPLE 4

The fluorination reaction of HCFC-133a was carried out in the same way as in Reaction Example 3 except that the reaction pressure was set to 4 $kg/cm^2G$. The results are shown in Table 1.

TABLE 1

Fluorination reaction result of HCFC-133a

| | Reaction pressure | 134a yield (%) | 134a selectivity (%) |
|---|---|---|---|
| Reaction Example 1 | atmos.* | 20.2 | 99.3 |
| Reaction Example 2 | 4 $kg/cm^2G$ | 19.8 | 99.4 |
| Comparative Reaction Example 1 | atmos.* | 20.5 | 99.1 |
| Comparative Reaction Example 2 | 4 $kg/cm^2G$ | 15.0 | 99.4 |
| Reaction Example 3 | atmos.* | 20.3 | 99.2 |
| Reaction Example 4 | 4 $kg/cm^2G$ | 17.8 | 99.3 |

*: atmospheric pressure

In Table given above, 134a yield and 134a selectivity represent yield and selectivity to HFC-134a, respectively.

It can be understood from the result shown in Table 1 that there was no significant difference in the yield of HFC-134a even when In was added or was not added at the atmospheric pressure, but when the reaction pressure became high (4 $kg/cm^2G$), the catalyst containing In added thereto provided a higher yield (compare Reaction Example 2 with Comparative Reaction Example 2). This indicates that the combination of In and Cr could overcome the negative effect of the pressure which could be observed on the catalyst comprising Cr alone.

REACTION EXAMPLES 5 to 10

The fluorination reactions of HCFC-133a were carried out in the same way as in Reaction Example 2 except that the catalysts prepared in Preparation Examples 3 to 8 were used, respectively. The results are shown in Table 2.

TABLE 2

Fluorination reaction result of HCFC-133a

| | Catalyst used | 134a yield (%) | 134a selectivity (%) |
|---|---|---|---|
| Reaction Example 5 | Prep. Example 3 | 20.7 | 99.3 |
| Reaction Example 6 | Prep. Example 4 | 16.1 | 99.4 |
| Reaction Example 7 | Prep. Example 5 | 15.3 | 99.3 |
| Reaction Example 8 | Prep. Example 6 | 20.3 | 99.4 |
| Reaction Example 9 | Prep. Example 7 | 20.1 | 99.3 |
| Reaction Example 10 | Prep. Example 8 | 19.3 | 99.3 |

In Table 2 above, 134a yield and 134a selectivity represent yield and selectivity to HFC-134a, respectively.

REACTION EXAMPLE 11

The fluorination reaction of dichloromethane with HF was carried out by packing 30 ml of the catalyst prepared in Preparation Example 3 into an Inconel reaction tube under the following reaction condition. An outlet gas of the reaction tube was blown into a trap of an aqueous KOH solution which was heated, and unreacted HF and resulting HCl were removed. The gas composition was analyzed by gas chromatograph.

temperature: 190° C.
pressure: atmospheric pressure molar ratio: 6

SV: 1,500 h$^{-1}$

Unreacted dichloromethane was 39%, and the yields of the principal reaction products were as follows:

HFC-32: 52%, HCFC-31: 8%

REACTION EXAMPLE 12

The fluorination reaction of HCFC-123 with HF was carried out by packing 30 ml of the catalyst prepared in Preparation Example 3 into an Inconel reaction tube under the following reaction condition. An outlet gas of the reaction tube was blown into a trap of an aqueous KOH solution, and unreacted HF and resulting HCl were removed. The gas composition was analyzed by gas chromatograph.

temperature: 325° C.

pressure: 4 kg/cm$^2$G molar ratio: 6

SV: 1,000 h$^{-1}$

Unreacted HCFC-123 was 10%, and the yields of the principal reaction products are as follows.

HFC-125: 60.6%, HCFC-124: 24.5%

As described above, when the fluorination reaction of a halogenated hydrocarbon is carried out by HF using the fluorination catalyst according to the present invention, an HFC can be obtained at a high yield even at an elevated pressure.

We claim:

1. A process for fluorinating a halogenated hydrocarbon comprising the step of: contacting a halogenated hydrocarbon with hydrogen fluoride in a gaseous phase in the presence of a fluorination catalyst, wherein the fluorination catalyst comprises indium, chromium, oxygen and fluorine as essential constituent elements thereof.

2. A process according to claim 1, wherein said halogenated hydrocarbon is a hydrogen-containing halogenated hydrocarbon.

3. A process according to claim 2, wherein said hydrogen-containing halogenated hydrocarbon is selected from dichloromethane, chlorofluoromethane, 1-chloro-2,2,2-trifluoroethane, 1,1-dichloro-2,2,2-trifluoroethane and 1-chloro-1,2,2,2-tetrafluoroethane.

4. A process according to claim 3, wherein said hydrogen-containing halogenated hydrocarbon is 1-chloro-2,2,2-trifluoroethane.

5. The process as claimed in claim 1, wherein the process produces at least one compound selected from the group consisting of difluoromethane, 1,1,1,2-tetrafluoroethane and pentafluoroethane.

6. The process as claimed in claim 1, wherein the molar ratio of hydrogen fluoride to the halogenated hydrocarbon is from 0.5 to 20.

7. The process as claimed in claim 1, wherein the reaction is conducted at a temperature of from 200° C. to 400° C.

8. The process as claimed in claim 1, wherein the reaction is conducted at a pressure of from atmospheric pressure to 20 kg/cm$^2$G.

9. The process as claimed in claim 8, wherein the pressure is from 1 to 20 kg/cm$^2$G.

10. The process as claimed in claim 9, wherein the pressure is from 1.5 to 20 kg/cm$^2$G.

11. The process as claimed in claim 1, wherein the atomic ratio of indium to chromium in the fluorination catalyst is from 0.005 to 0.6.

12. The process as claimed in claim 11, wherein the atomic ratio of indium to chromium in the fluorination catalyst is from 0.01 to 0.5.

13. The process as claimed in claim 12, wherein the atomic ratio of indium to chromium in the fluorination catalyst is from 0.01 to 0.3.

14. The process as claimed in claim 1, wherein the content of oxygen in the fluorination catalyst is from 1 to 25% by weight based on the weight of the catalyst.

15. The process as claimed in claim 1, wherein the fluorination catalyst further comprises at least one element selected from the group consisting of the elements of Groups 11, 12, 13 and 14 of the Long Form Periodic Table.

16. The process as claimed in claim 15, wherein the at least one element selected from the group consisting of the elements of Groups 11, 12, 13 and 14 of the Long Form of the Periodic Table and chromium in the fluorination catalyst are present in an atomic ratio of from 0.001 to 0.5.

17. The process as claimed in claim 15, wherein said at least one element is selected from the group consisting of copper, silver, gold, zinc, cadmium, mercury, aluminum, gallium, tin and lead.

* * * * *